United States Patent [19]
Thenappan et al.

[11] Patent Number: 5,969,198
[45] Date of Patent: Oct. 19, 1999

[54] PROCESS FOR THE PREPARATION OF 1,1,1,3,3-PENTAFLUOROPROPANE

[75] Inventors: Alagappan Thenappan, Cheektowaga; Michael Van Der Puy, Amherst; Hsueh S. Tung, Getzville, all of N.Y.

[73] Assignee: AlliedSignal Inc., Morristown, N.J.

[21] Appl. No.: 08/883,670

[22] Filed: Jun. 27, 1997

[51] Int. Cl.$^6$ .................................................. C07C 17/08
[52] U.S. Cl. ........................ 570/167; 570/168; 570/170
[58] Field of Search ................... 570/167, 170, 570/168

[56] References Cited

U.S. PATENT DOCUMENTS

| | | | |
|---|---|---|---|
| 4,990,701 | 2/1991 | Cassel et al. | 570/170 |
| 5,045,634 | 9/1991 | Fernandez et al. | 570/170 |
| 5,574,192 | 11/1996 | VanDerPuy et al. | 570/167 |
| 5,616,819 | 4/1997 | Boyce et al. | 570/167 |

FOREIGN PATENT DOCUMENTS

| | | |
|---|---|---|
| 0 611 744 A1 | 3/1994 | European Pat. Off. |
| WO 95/04022 | 2/1995 | WIPO . |

OTHER PUBLICATIONS

Maynard, John T., "The Synthesis of Highly Fluorinated Compounds by Use of Potassium Fluoride in Polar Solvents", E.I. du Ponte de Nemours & Co., vol. 28, Jan., 1963, pp. 112–115.

English Abstract WO 94/29251 (1994).

English Abstract 0 611 744 A1 (1994).

*Primary Examiner*—Alan Siegel
*Attorney, Agent, or Firm*—Jay P. Friedenson

[57] ABSTRACT

A process for preparing 1,1,1,3,3-pentafluoropropane from a hydrochlorocarbon of the formula $C_3H_yCl_x$, wherein x is an integer from 3 to 5, y is an integer from 1 to 3, x+y=4, 6, or 8, and x−y=2 is provided.

24 Claims, No Drawings

PROCESS FOR THE PREPARATION OF 1,1,1, 3,3-PENTAFLUOROPROPANE

FIELD OF THE INVENTION

The invention relates to the preparation of 1,1,1,3,3-pentafluoropropane. In particular the invention provides a process for preparing 1,1,1,3,3-pentafluoropropane from three carbon hydrochlorocarbon compounds.

BACKGROUND OF THE INVENTION

Hydrofluorocarbons ("HFC's") are of great interest due to their potential to replace ozone-depleting chlorofluorocarbons ("CFC's") and hydrochlorofluorocarbons ("HCFC's") in a variety of applications including refrigerant, solvent, foam blowing, aerosol propellant, and heat transfer applications. Among the HFC's, 1,1,1,3,3-pentafluoropropane ("HFC-245fa") has been identified as a foam blowing agent, an aerosol propellant, and a heat transfer agent as well as a possible replacement for dichlorodifluoromethane in refrigeration systems.

Methods for the preparation of HFC-245fa are known. For example, the catalytic hydrogenation of 1,1,1,3,3-pentafluoropropene with hydrogen in the presence of a palladium catalyst is disclosed in WO 94/29251. Hydrodechlorination of 3-chloro-1,1,1,3,3-pentafluoropropane with hydrogen over a reduction catalyst to produce HFC-245fa is disclosed in WO 95/04022. The preparation of HFC-245fa from di- or trichloropentafluoropropanes via hydrogenation is disclosed in EP 611 744. The reaction of vinyl chloride with carbon tetrachloride to produce $CCl_3CH_2CHCl_2$ ("HCC-240fa") followed by the fluorination of HCC-240fa with hydrogen fluoride in the presence of a fluorination catalyst to produce HFC-245fa is disclosed in U.S. Pat. No. 5,574,192. U.S. Pat. No. 5,616,819 discloses the uncatalyzed fluorination of a chlorinated olefin followed by the catalyzed fluorination of the resulting chlorofluoro intermediate to produce HFC-245fa.

Certain disadvantages are inherent in all of these methods. The hydrogenation of unsaturated pentafluoropropene and mono-, di-, and trichloropentafluoropropanes requires either or both high reaction temperatures and multiple steps to prepare the feed material. Additionally, the reaction exhibits poor selectivity for the desired product. The fluorination of HCC-240fa with an antimony pentafluoride fluorination catalyst is highly corrosive to metallic reactors. The fluorination of chlorinated olefins in the presence of catalysts produces a tarry residue and the desired product is formed in poor yields.

Therefore, a need exists in the art for new methods for producing HFC-245fa that overcomes some of these disadvantages.

DESCRIPTION OF THE INVENTION AND PREFERRED EMBODIMENTS

The present invention provides a fluorination process for preparing 1,1,1,3,3-pentafluoropropane, or HFC-245fa, from a hydrochlorocarbon ("HCC"). Generally, the process of the invention comprises the step of fluorinating an HCC of the formula $C_3H_yCl_x$, wherein x is an integer from 3 to 5, y is an integer from 1 to 3, x+y=4, 6, or 8, and x−y=2, under conditions suitable to produce a HFC-245fa product stream comprising HFC-245fa product, reaction intermediates, and unreacted starting materials. More particularly, the process of the invention comprises the step of fluorinating an HCC of the formula $C_3H_yCl_x$, wherein x is an integer from 3 to 5, y is an integer from 1 to 3, x+y=4, 6, or 8, and x−y=2, in the presence of effective amounts of a metal fluoride fluorinating agent and a solvent or effective amounts of hydrogen fluoride and a catalytic amount of a fluorination catalyst under conditions suitable to produce a HFC-245fa product stream.

It is known that fluoride ions have high heats of hydration and hydrated fluoride ions are poor nucleophiles in substitution reactions. Therefore, water must be substantially excluded from the fluorination reactions of the invention, the fluorinating agent must be dried prior to use, and the reaction carried out under substantially anhydrous conditions in processes of the invention.

Suitable HCC'S useful in the process of the invention include, without limitation, $CHCl_2CHClCHCl_2$ ("HCC-240da"), E and Z isomers of $CHCl_2CCl=CHCl$ ("HCC-1230xd"), $CCl_2=C=CHCl$ ("HCC-2220"), $CCl_3CH_2CHCl_2$ ("HCC-240fa"), E and Z isomers of $CCl_3CH=CHCl$ ("HCC-1230zd"), $CHCl_2CH=CCl_2$ ("HCC-1230za"), and mixtures thereof. Preferably, E and Z isomers of HCC-1230xd are used. HCC-240da and HCC-1230xd are commercially available or may be prepared from chloroform and 1,2-dichloroethene. The preparation of HCC-240fa is disclosed in U.S. Pat. No. 5,574,192. The dehydrochlorination of HCC-1230xd will produce HCC-2220 and dehydrochlorination of HCC-240fa will produce HCC-1230zd and HCC-1230za. The dehydrochlorination of chlorocarbons and hydrochlorocarbons is well known in the art.

In one embodiment of the invention, the HCC is fluorinated with a metal fluoride fluorinating agent. Useful metal fluoride fluorinating agents include, without limitation, potassium fluoride, sodium fluoride, cesium fluoride, rubidium fluoride, lithium fluoride, ammonium fluoride, and silver fluoride. Preferably the metal fluoride fluorinating agent is potassium fluoride. The metal fluoride fluorinating agents useful in the invention are commercially available.

The fluorination reaction of the invention using a metal fluoride is carried out in the presence of a solvent. Preferably, the solvent is a polar solvent. Generally, the metal fluoride fluorination reaction may be carried out at temperatures of about 150 to about 250° C., preferably at temperatures of about 175 to about 225° C. Therefore, the solvent should have a boiling point of greater than about 150° C., preferably of greater than about 175° C.

The solvent also must be stable at high temperatures and have a dielectric constant such that it is able to dissolve the quantity of alkali metal fluoride fluorinating agent desired for use in the reaction. Examples of suitable solvents include, without limitation, N-methyl pyrrolidone, dimethyl sulfone, dimethyl sulfoxide, formamide, N-methylacetamide, N-methylformamide, dimethyl formamide, glycols, and glymes. Preferably, N-methyl pyrrolidone is used. The amount of solvent used will depend on the solubility of the metal fluoride fluorinating agent in the solvent and is readily determinable by one ordinarily skilled in the art. In any case, an effective amount of solvent is an amount sufficient to dissolve the metal fluoride used. The solvent is recyclable.

In another embodiment of the invention, hydrogen fluoride and a fluorinating catalyst are used to fluorinate the HCC. The hydrogen fluoride used is substantially anhydrous, having a water content of less than about 0.05 weight percent, preferably less than about 0.02 weight percent, which hydrogen fluoride is commercially available. Any suitable fluorination catalyst may be used. Suitable catalysts include, without limitation pentavalent antimony, arsenic, niobium, tantalum, tungsten, and molybdenum halides and mixed halides and tetravalent titanium and tin halides and mixed halides, and mixtures thereof. The halides are commercially available and the mixed halides may be generated in situ.

An amount of catalyst is used sufficient to catalyze the fluorination reaction. The amount of catalyst, generally, may be about 2 to about 80 weight percent, preferably about 5 to about 20, more preferably about 8 to about 15 weight percent based on the amount of HCC. For vapor phase embodiments of the process, the catalyst may be supported on an inert support such as activated carbon.

In still another embodiment, both a metal fluoride and hydrogen fluoride may be used to fluorinate the HCC in the presence of a solvent. The solvent, temperature and pressures for such a reaction are those described for the metal fluoride/solvent embodiment.

In the fluorination reactions of the invention, an effective amount of the metal fluoride and/or hydrogen fluoride is used. Based on reaction stoichiometry, an effective amount may be a molar ratio of the metal fluoride and/or hydrogen fluoride to HCC that is at least equal to the number of chlorine atoms to be replaced. Preferably, an excess is used. In a preferred embodiment, the molar ratio of metal fluoride and/or hydrogen fluoride to HCC is from at least about 5:1 to about 20:1. More preferably, the ratio is from at least about 5:1 to about 10:1.

Generally, the reaction temperature of the embodiment using hydrogen fluoride may be from about 50° C. to about 300° C. In a preferred embodiment, temperatures of from about 100° to about 250° C., more preferably from about 125° to about 225° C. may be used.

The reaction time for either process embodiment, generally, may be from about 1 second to about 24 hours. In a preferred embodiment, the reaction is carried out in from about 1 second to about 12 hours, more preferably from about 1 second to about 4 hours.

The reaction pressure is not critical. However, the metal fluoride reaction is most conveniently carried out at atmospheric pressure. The reaction pressure for the hydrogen fluoride embodiment will vary depending on the quantity of hydrogen fluoride used, hydrogen chloride generated, and conversion of the organics. Convenient operating pressures for this embodiment range from about 50 to about 600 psig, preferably, from about 50 to about 400 psig. The pressure may be adjusted by continuously removing hydrogen chloride and volatile products from the reactor by distillation.

The fluorination reactions of the invention produce a HFC-245fa product stream, which stream contains HFC-245fa product, unreacted starting materials, intermediates, and byproducts. The volatile HFC-245fa product, with a boiling point of 15° C., may be recovered from the product stream by any convenient separation method. The intermediates in the product stream, which may include without limitation HFC-1234ze, HCFC-1233 isomers, HCFC-1232 isomers and HCFC-1231 isomers, preferably are recycled to the reactor. HFC-1234ze isomers include $CF_3CH\!=\!CHF$. HCFC-1233 isomers include $CF_3CCl\!=\!CH_2$, $CF_3CH\!=\!CHCl$, and $C_3H_2F_3Cl$. HCFC-1232 isomers include $CF_2HCCl\!=\!CHCl$ and $C_3H_2F_2Cl_2$. HCFC-1231 isomers include $CHFClCCl\!=\!CHCl$.

The processes of the invention may be carried out as a batch or continuous process, but preferably is carried out as a continuous process. In the continuous process, the HFC-245fa is removed from the reactor as it is formed. The reactor may be constructed of any suitable known material that is capable of withstanding the reaction temperatures and reactants. Suitable reactors include, without limitation, stainless steel, nickel, MONEL™, INCONEL™, HASTELLOY™ and lined reactors. Glass or glass-lined reactors may be used for the metal fluoride process embodiments.

The fluorination of octa-, hepta-, and hexachloropropanes and penta-, and hexachloropropenes with potassium fluoride is reported in Maynard, John T., 28 Jl of Organic Chem., 112–115 (1963). The Maynard article discloses that the fluorination of $CHCl_2CHClCCl_3$, $CHCl_2CCl_2CHCl_2$, and $CHCl_2CCl\!=\!CCl_2$ give $CF_3CH_2CF_3$ as the major product in a yield of approximately 20 percent. Tetrachloroallene, $CCl_2\!=\!C\!=\!CCl_2$ ("CC-2210") is disclosed as an intermediate in the fluorination reaction and degradation and resinification of the allene the cause of the poor yields. Thus, given the Maynard disclosure, one would expect the processes of the present invention to suffer similarly poor yields. However, it is an unexpected discovery of the invention that fluorination processes of the invention proceeds without the problems disclosed by Maynard.

Additionally, heretofore the liquid phase fluorination of E and Z isomers of HCC-1230xd with hydrogen fluoride and a catalyst were believed to produce only the difluoro compound $CHF_2CCl\!=\!CHCl$ ("HCFC-1232xd"). It is another discovery of the invention that an E/Z isomeric mixture of HCC-1230xd may be fluorinated to produce HFC-245fa in high yield.

The invention will be clarified further by a consideration of the following, non-limiting examples.

EXAMPLES

Fluorinations were carried out in a three-necked, glass flask equipped with stirrer, thermometer, gas inlet tube, and a Claisen still head carrying a dropping funnel for addition of the organic material and a vacuum take-off connected to traps cooled with dry ice for the collection of low boiling products. Reagent grade potassium fluoride was dried at least 2 hours in a 150° C. vacuum oven and anhydrous N-methyl pyrrolidone, from Aldrich Chemicals, was used. In the general procedure, a 100% excess of potassium fluoride over the stoichiometric quantity was used. Potassium fluoride and the solvent were brought to 195° C. and a gentle flow of nitrogen was used to remove any volatile products. The hydrochlorocarbon was added over a 1–3 hour period and, for solid organic materials, it was introduced as a concentrated solution in the solvent. If the HCC had a low boiling point, less than about 100° C., then a water-cooled condenser was inserted below the Claisen head to reflux the reactant. Products were distilled, collected in dry ice traps, and analyzed by GC, NMR, and GC-MS.

EXAMPLE 1

280 mL N-methyl pyrrolidone and 101.0 g (1.74 moles) potassium fluoride were charged to a 500 mL flask and the resultant slurry heated to 195° C. with vigorous stirring. After the reaction mixture temperature equilibrated at 192° C., 36.1 g (0.20 moles) of a E & Z isomeric mixture of 1,1,2,3-tetrachloropropene, HCC-1230xd, were added dropwise over 2 hrs. The product distilled as the hydrochlorocarbon was added and its formation was complete 0.5 hr after addition was completed. Heating at 192° C. with stirring was continued for an additional 2 hrs. There was obtained 3.1 g of product mixture. The distilled product and the reaction mixture were analyzed by GC-MS and GC. GC-MS analysis indicated: $CF_3CH\!=\!CHF$ (57.6%);

$CF_3CH_2CHF_2$ (1.7%), a mixture of isomeric chlorotrifluoropropenes, HCFC-1233 (25.5%), a mixture of isomeric dichlorodifluoropropenes, HCFC-1232 (10.5%), $C_3HClF_2$ (3.0%) and trichlorofluoropropene, HCFC-1231xd (0.5%).

The process of Example 1 demonstrates the production of HFC-245fa along with the intermediates 1234, 1233, 1232, and 1231 which intermediates may be recycled to produce additional HFC-245fa.

EXAMPLE 2

The procedure of Example 1 is used. 43.3 g (0.2 mole) HCC-240da are added to a mixture of 116.0 (2.0 moles) potassium fluoride in 320 mL N-methyl pyrrolidone over 2 hr at 195° C. with vigorous stirring. A product mixture of $CF_3CH_2CHF_2$, $CF_3CH=CHF$, HCFC-1233, HCFC-1232, and HCFC-1231 is produced.

EXAMPLE 3

The procedure of Example 1 is used. 54.1 g (0.25 mole) HCC-240fa are added to a mixture of 145.0 g (2.5 moles) potassium fluoride dissolved in 400 mL N-methyl pyrrolidone over 2 hr at 200° C. with vigorous stirring. A product mixture of $CF_3CH_2CHF_2$, $CF_3CH=CHF$, HCFC-1233, HCFC-1232, and HCFC-1231 is produced.

EXAMPLE 4

The procedure of Example 1 is used. 36.0 g (0.20 mole) HCC-1230zd are added to a mixture of 101.0 g (1.74 moles) potassium fluoride in 280 mL N-methyl pyrrolidone over 2 hr at 190° C. with vigorous stirring. A product mixture of $CF_3CH_2CHF_2$, $CF_3CH=CHF$, HCFC-1233, HCFC-1232, and HCFC-1231 is produced.

EXAMPLE 5

The procedure of Example 1 is used. 54.0 g (0.30 mole) HCC-1230za are added to a mixture of 146.2 g (2.52 moles) potassium fluoride in 406 mL N-methyl pyrrolidone over 2 hr at 190° C. with vigorous stirring. A product mixture of $CF_3CH_2CHF_2$, $CF_3CH=CHF$, HCFC-1233, HCFC-1232, and HCFC-1231 is produced.

EXAMPLE 6

A 600 mL Hastelloy™ autoclave equipped with a magnetic stir drive and a column condenser assembly is charged with 12.9 g (0.036 moles) tantalum pentachloride, 64.7 g (3.24 moles) anhydrous hydrogen fluoride, and 45.0 g (0.25 mole) HCC-1230xd. When the resultant mixture is heated to 120° C., in 30 min, and maintained at that temperature for 4.5 h with stirring, a product mixture containing $CF_3CH=CHF$, $CF_3CH_2CHF_2$, $C_3HClF_2$, and a mixture of isomeric chlorotrifluoropropenes, dichlorodifluoropropene, and trichlorofluoropropenes is produced.

EXAMPLE 7

The procedure of Example 6 is used except that 45.0 g (0.25 mole) HCC-1230za re added to a mixture of 10.8 g (0.036 mole) antimony pentachloride and 26.2 g (1.31 moles) anhydrous hydrogen fluoride is used. A product mixture of $CF_3CH=CHF$, $CF_3CH_2CHF_2$, $C_3HClF_2$, and a mixture of isomeric chlorotrifluoropropenes, dichlorodifluoropropenes, and trichlorofluoropropenes is produced.

What is claimed is:

1. A process comprising the step of fluorinating a hydrochlorocarbon of the formula $C_3H_yCl_x$, wherein x is an integer form 3 to 5, y is an integer from 1 to 3, x+y=4, 6, or 8, and x−y=2, under conditions suitable to produce a 1,1,1,3,3-pentafluoropropane product stream comprising 1,1,1,3,3-pentafluoropropane product, unreacted starting materials, and reaction intermediates, wherein the fluorinating step comprises fluorinating the hydrochlorocarbon in the presence of effective amounts of a metal fluoride fluorinating agent and a solvent wherein the metal fluoride is selected from the group consisting of potassium fluoride, sodium fluoride, cesium fluoride, rubidium fluoride, lithium fluoride, ammonium fluoride and silver fluoride.

2. The process of claim 1 wherein the hydrochlorocarbon is selected from the group consisting of $CHCl_2CHClCHCl_2$, E and Z isomers of $CHCl_2CCl=CHCl$, $CCl_2=C=CHCl$, $CCl_3CH_2CHCl_2$, E and Z isomers of $CCl_3CH=CHCl$, $CHCl_2CH=CCl_2$, and mixtures thereof.

3. The process of claim 2 wherein the hydrochlorocarbon is E and Z isomers of $CHCl_2CCl=CHCl$.

4. The process of claim 1 wherein the metal fluoride is potassium fluoride.

5. The process of claim 1 wherein the solvent is selected from the group consisting of N-methyl pyrrolidone, dimethyl sulfone, dimethyl sulfoxide, formamide, N-methylacetamide, N-methylformamide, dimethyl formamide, glycols, and glymes.

6. The process of claim 4 wherein the solvent is selected from the group consisting of N-methyl pyrrolidone, dimethyl sulfone, dimethyl sulfoxide, formamide, N-methylacetamide, N-methylformamide, dimethyl formamide, glycols, and glymes.

7. The process of claim 5 wherein the solvent is N-methyl pyrrolidone.

8. The process of claim 6 wherein the solvent is N-methyl pyrrolidone.

9. A process comprising the step of fluorinating a hydrochlorocarbon of the formula $C_3H_yCl_x$, wherein x is an integer form 3 to 5, y is an integer from 1 to 3, x+y=4, 6, or 8and x−y=2, under conditions suitable to produce a 1,1,1,3,3-pentafluoropropane product stream comprising 1,1,1,3,3-pentafluoropropane product, unreacted starting materials, and reaction intermediates, wherein the fluorinating comprises fluorinating a hydrochlorocarbon selected from the group consisting of $CHCl_2CHClCHCl_2$, E and Z isomers of $CHCl_2CCl=CHCl$, $CCl=C=CHCl$, E and Z isomers of $CCl_3CH=CHCl$, $CHCl_2CH=CCl_2$, and mixtures thereof in the presence of an effective amount of hydrogen fluoride and a catalytic amount of a fluorination catalyst.

10. The process of claim 9 wherein the hydrochlorocarbon is E and Z isomers of $CHCl_2CCl=CHCl$.

11. The process of claim 9 wherein the fluorination catalyst is selected from the group consisting of pentavalent antimony, arsenic, niobium, tantalum, tungsten, and molybdenum halides and mixed halides, tetravalent titanium and tin halides and mixed halides, and mixtures thereof.

12. The process of claim 1 or 2 further comprising the step of recovering the 1,1,1,3,3-pentafluoropropane product from the product stream.

13. The process of claim 9 further comprising the step of recovering the 1,1,1,3,3-pentafluoropropane product from the product stream.

14. The process of claim 1 or 2 further comprising recycling the reaction intermediates comprising HFC-1234ze, HCFC-1233 isomers, HCFC-1232 isomers and HCFC-1231 isomers to the fluorinating step.

15. The process of claim 9 further comprising recycling the reaction intermediates comprising HFC-1234ze, HCFC-1233 isomers, HCFC-1232 isomers and HCFC-1231 isomers to the fluorinating step.

16. A process comprising the step of fluorinating a hydrochlorocarbon of the formula $C_3H_yCl_x$, wherein x is an integer from 3 to 5, y is an integer from 1 to 3, x+y=4, 6, or 8, and x−y=2, in the presence of effective mounts of a metal fluoride selected from the group consisting of potassium fluoride, sodium fluoride, cesium fluoride, rubidium fluoride, lithium fluoride, ammonium fluoride, and silver fluoride and a solvent selected from the group consisting of N-methyl pyrrolidone, dimethyl sulfone, dimethyl sulfoxide, formamide, N-methylacetamide, N-methylformamide, dimethyl formamide, glycols, and glymes under conditions suitable to produce a 1,1,1,3,3-pentafluoropropane product stream comprising 1,1,1,3,3-pentafluoropropane product, unreacted starting materials, and reaction intermediates.

17. The process of claim 16 wherein the hydrochlorocarbon is selected from the group consisting of $CHCl_2CHClCHCl_2$, E and Z isomers of $CHCl_2CCl=CHCl$, $CCl_2=C=CHCl$, $CCl_3CH_2CHCl_2$, E and Z isomers of $CCl_3CH=CHCl$, $CHCl_2CH=CCl_2$, and mixtures thereof.

18. The process of claim 17 wherein the hydrochlorocarbon is E and Z isomers of $CHCl_2CCl=CHCl$.

19. The process of claims 16, 17, or 18 wherein the metal fluoride is potassium fluoride and the solvent is N-methyl pyrrolidone.

20. The process of claims 16, 17, or 18 further comprising recycling the reaction intermediates comprising HFC-1234ze, HCFC-1233 isomers, HCFC-1232 isomers and HCFC-1231 isomers to the fluorinating step.

21. A process comprising the steps of:
fluorinating a hydrochlorocarbon of the formula $C_3H_yCl_x$, wherein x is an integer from 3 to 5, y is an integer from 1 to 3, x+y=4, 6, or 8, and x−y=2, in the presence of effective amounts of potassium fluoride and a solvent selected from the group consisting of N-methyl pyrrolidone, dimethyl sulfone, dimethyl sulfoxide, formamide, N-methylacetamide, N-methylformamide, dimethyl formamide, glycols, and glymes at a temperature from about 150 to about 250° C. and for a reaction time of from about 1 second to about 24 hours to produce a 1,1,1,3,3-pentafluoropropane product stream comprising 1,1,1,3,3-pentafluoropropane product, unreacted starting materials and reaction intermediates comprising HFC-1234ze, HCFC-1233 isomers, HCFC-1232 isomers and HCFC-1231 isomers; and
recycling the reaction intermediates to the fluorinating step.

22. The process of claim 21 wherein the hydrochlorocarbon is selected from the group consisting of $CHCl_2CHClCHCl_2$, E and Z isomers of $CHCl_2CCl=CHCl$, $CCl_2=C=CHCl$, $CCl_3CH_2CHCl_2$, E and Z isomers of $CCl_3CH=CHCl$, $CHCl_2CH=CCl_2$, and mixtures thereof.

23. The process of claim 21 wherein the hydrochlorocarbon is E and Z isomers of $CHCl_2CCl=CHCl$.

24. The process of claim 21 wherein the solvent is N-methyl pyrrolidone.

* * * * *